United States Patent [19]

Onsager

[11] 3,954,831
[45] May 4, 1976

[54] DIMERIZATION PROCESS

[75] Inventor: Olav Torgeir Onsager, Suffern, N.Y.

[73] Assignee: Halcon International, Inc., New York, N.Y.

[22] Filed: Dec. 30, 1974

[21] Appl. No.: 537,295

[52] U.S. Cl. .......................................... 260/465.8 D
[51] Int. Cl.² ...................................... C07C 120/00
[58] Field of Search .............................. 260/465.8 D

[56] References Cited
UNITED STATES PATENTS

| | | | |
|---|---|---|---|
| 3,484,475 | 12/1969 | Cornforth et al. | 260/465.8 D |
| 3,641,106 | 2/1972 | Cornforth et al. | 260/465.8 D |
| 3,733,351 | 5/1973 | Watanabe et al. | 260/465.8 D |

Primary Examiner—Joseph P. Brust
Attorney, Agent, or Firm—William C. Long; David Dick; Riggs T. Stewart

[57] ABSTRACT

Acrylonitrile is dimerized by reaction in the presence of a catalyst consisting essentially of (a) at least one metal compound of the formula $M(X)_n$ wherein M is Zn or Co, X is an anion derived from an alkyl or aryl sulfonic acid or from a carboxylic acid containing at least two carbon atoms which is substituted by at least one of the groups, —F, —Cl, —Br, —I and —CN in the α-C-position relative to the acid group and $n$ is a number equal to the valence of the metal M divided by the number of acid equivalents of X and (b) at least one nitrogen-containing Lewis Base which is (1) a tertiary monoamine of the formula

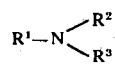

wherein $R^1$, $R^2$, and $R^3$ are the same or different and each is an alkyl, cycloalkyl, benzyl or aryl radical; or (2) a tertiary di- or poly-functional amine which contains at least two Lewis Base nitrogen groups separated from each other by at least one carbon atom, and which are (a) N-disubstituted amino groups wherein each N-substituent is the same or different and is an alkyl, cycloalkyl, benzyl or aryl radical, or (b) N-heterocyclic groups containing 3 to 20 carbon atoms; or (3) an N-substituted heterocyclic amine containing 3 to 20 carbon atoms in the heterocyclic ring wherein the N-substituent is an alkyl, cycloalkyl, benzyl or aryl radical.

9 Claims, No Drawings

DIMERIZATION PROCESS

This invention relates to the dimerization of nitriles of α,β-unsaturated carboxylic acids and is more particularly concerned with the dimerization of acrylonitrile.

The dimerization of certain α,β-unsaturated carboxylic acid derivatives is a known reaction. For example, acrylonitrile can be dimerized in the presence of a catalyst to produce 2-methylene glutaronitrile (2-MGN). Such dimerization is commonly referred to as "head-to-tail" dimerization since in the dimer the α-carbon atom of one monomer molecule is attached to the β-carbon atom of the other monomer molecule. Various tertiary phosphines, certain types of cyclic tertiary amines having at least one nitrogen atom common to two or three rings, e.g., triethylenediamine (British Pat. No. 1,168,774) and a wide variety of metal carbonyls are known to be suitable for use as catalysts in this reaction. Furthermore, the use of a catalyst system composed of at least one metal halide of the formula $MX_n$ in which M is zinc, aluminum, titanium, vanadium, iron or cobalt, X is a halogen and $n$ is a number equal to the valence of the metal M and at least one trialkylamine of the formula

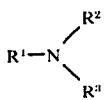

in which $R^1$, $R^2$, and $R^3$ are alkyl groups, is known (British Pat. No. 1,256,392 and U.S. Pat. No. 3,733,351).

The object of the present invention is to provide an improved process for the dimerization of acrylonitrile characterized by the use of a novel catalyst system.

It is a further object of the invention to provide a process of the character indicated which is particularly applicable to the head-to-tail dimerization of acrylonitrile to produce 2-methylene glutaronitrile.

In accordance with the invention, acrylonitrile is dimerized in the presence of a catalyst which consists essentially of (a) at least one metal compound of the formula $M(X)_n$ wherein M is Zn or Co, X is an anion derived from an alkyl or aryl sulfonic acid or from a carboxylic acid containing at least two carbon atoms which is substituted by at least one of the groups —F, —Cl, —Br, —I and —CN in the α-C-position relative to the acid group and $n$ is a number equal to the valence of the metal M divided by the number of acid equivalents of X, and (b) at least one nitrogen-containing Lewis Base which is (1) a tertiary monoamine of the formula

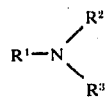

wherein $R^1$, $R^2$, and $R^3$ are the same or different and each is an alkyl, cycloalkyl, benzyl or aryl radical; or (2) a tertiary di- or poly-functional amine which contains at least two Lewis Base nitrogen groups separated from each other by at least one carbon atom, and which are (a) N-disubstituted amino groups wherein each N-substituent is the same or different and is an alkyl, cycloalkyl, benzyl or aryl radical or (b) N-heterocyclic groups containing 3 to 20 carbon atoms; or (3) an N-substituted heterocyclic amine containing 3 to 20 carbon atoms in the heterocyclic ring wherein the N-substituent is an alkyl, cycloalkyl, benzyl or aryl radical. Preferably, the alkyl radicals have 1 to 20 carbon atoms, the benzyl radicals have 7 to 20 carbon atoms and the aryl radicals have 6 to 20 carbon atoms. In addition, all the radicals, including the heterocyclic rings, may contain non-reactive groups, e.g., nitrile, ether and ester-groups.

The alkyl, aryl or alkaryl groups of the sulfonic acid of the (a) component may be substituted with or include non-reactive groups such as nitro groups, halogen groups, phenyl groups and alkyl groups. Preferably, the aryl groups have 1 to 3 rings and the alkyl substituents contain up to 20 carbon atoms.

Typical examples of the (a) component having the formula $M(X)_n$ include $Zn(dichloroacetate)_2$, $Zn(tribromoacetate)_2$, $Zn(monofluoroacetate)_2$, $Zn(trifluoroacetate)_2$, $Zn(iododifluoroacetate)_2$, $Zn(Heptafluorobutyrate)_2$, $Zn(octafluoroadipate)$, $Zn(cyanoacetate)_2$, $Zn(phenyldifluoroacetate)_2$, $Zn(trifluoromethanesulfonate)_2$, $Zn(1$-heptane sulfonate$)_2$, $Zn(1,2$ ethanedisulfonate$)$, $Zn(benzenesulfonate)_2$, $Zn(2,4,6$-trinitrobenzene sulfonate$)_2$, $Zn(m$-benzenedisulfonate$)$, $Zn(2,4$ dimethylbenzenesulfonate$)_2$, $Zn(β$-naphthalene sulfonate$)_2$, $Zn(2$-anthraquinonesulfonate$)_2$, $Co(trichloroacetate)_2$, $Co(trifluoroacetate)_2$, and $Co(p$-cumenesulfonate$)_2$. The preferred metal is zinc and the preferred anions X are those which are derived from aryl sulfonic acids and tri halosubstituted acetic acid, e.g., trichloroacetic acid and trifluoroacetic acid.

The metal salts of the (a) component are readily prepared in conventional manner, e.g., by the reaction of the metal oxide with the sulfonic acid or carboxylic acid corresponding to the anion (X). For example, the metal sulfonates are produced in accordance with the following equation:

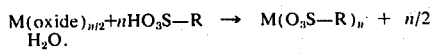

This method leads to pure $M(O_3S—R)_n$ when water is removed from the reaction mixture. The metal salts of the carboxylic acids are similarly prepared. Most suitably the acid which provides the anion (X) is one having a pK value below 3.0.

Typical Lewis Bases suitable for use as the (b) component of the catalyst system of the invention include tertiary monoamines such as trimethylamine dimethylethylamine, triethylamine, tripropylamine, trihexylamine, methyldiethylamine, 3-diethylaminopropionitrile, dimethylcyclohexylamine, tricyclohexylamine, triisobutylamine, N,N-diethylaniline, N,N-dimethylparatolylamine, N,N-dipropylaniline, N,N-diethylmesitylamine, N,N-dimethylbenzylamine, N,N-diethylbenzylamine, and N,N-dicyclohexylbenzylamine; tertiary di- and poly-amines such as N,N, $N^1$, $N^1$ tetraethyl-1, 6-hexanediamine, N,N-diethylaminomethyl-polystyrene and p-(N,N-diethylamino)-N, N-diethylaniline, methylenedipiperidine; tertiary heterocyclic amines such as N-methylpiperidine, N-cyclohexylpiperidine, N-phenylpiperidine, N-benzylpiperidine, N-ethylmorpholine, N,$N^1$-dimethylpiperazine, and N-methylpyrrolidine. The most preferred Lewis Bases are those which are tertiary monoamines or heterocyclic amines.

It should be understood that the specific (a) and (b) catalyst components identified above are merely representative of suitable compounds and the invention is not limited to these specific compounds but includes like compounds within the generic definition of the (a) and (b) compounds.

The molar ratio between the Lewis base component and the metal salt component can vary widely. In general, the Lewis base/metal salt mole ratio is from 0.1:1 to 25:1, preferably 0.5:1 to 20:1.

The concentration of the metal salt in the reaction zone is suitably selected to give a practical rate of reaction. It has been found that the rate of reaction increases with increasing metal salt concentrations. In general, the metal salt concentration is advantageously from 0.5 to 20 wt. %, the preferred concentration being from 1.0 to 15 wt. %, based on the weight of the liquid-phase reaction mixture.

The catalyst system may be soluble or (at least in part) insoluble in the reaction mixture. A solvent can be used, if desired, but is not necessary for carrying out the dimerization reaction. Preferred solvents are aliphatic or aromatic nitriles, hydrocarbons, especially aromatic hydrocarbons, chlorohydrocarbons, ethers, sulfoxides and like organic solvents inert in the dimerization reaction. Examples of preferred solvents include acetonitrile, propionitrile, benzonitrile, hexane, hexadecane, benzene, p-xylene, o-dichlorobenzene, sulfolane and dimethylsulfoxide. The amount of solvent, when used, is suitably 5–80 wt. % of liquid reaction mixture.

The two catalyst components can be added separately to the reaction zone or they can be premixed before addition. Furthermore, if desired, one or both components can be dissolved in an inert solvent and fed to the reaction zone in the form of a solution.

The pressure and temperature are selected so as to maintain the monomer being dimerized in the liquid phase during the reaction. In general, the temperature is within the range of from 10° to 150°C, the most preferred temperature being from 20° to 100°C. The pressure will, of course, vary with the temperature and typically will be within the range of 0.1 atm. to 100 atm., generally 1 atm. to 10 atm.

If desired, a polymerization inhibitor for the monomer can be used. Such inhibitors are well known and typical inhibitors include hydroquinone, methylene blue, and p-nitrosodimethylaniline. Very small amounts of inhibitor can be employed, e.g., 5 to 1000 ppm. based on the weight of the monomer.

The process according to the invention can be carried out as a batch process or in continuous fashion. The residence time is selected to give at least 1 wt. % dimer product in the liquid-phase reaction mixture. The concentration of dimer is readily determined by conventional analytical procedures such as gas/liquid chromatography. In general, residence times of less than 10 hours are employed, the preferred residence time being less than 6 hours. In general, a residence time of at least 5 minutes is normally employed.

The dimer product is recovered from the reaction product by conventional means such as distillation or solvent extraction. The catalyst can be reused, if desired, by recycling either or both of the two components, after the dimer and unreacted monomer have been separated from them.

In order to obtain improved rates of reaction the reaction system should be kept substantially anhydrous.

Preferred Lewis Bases and preferred salts have been indicated, but the preferred catalyst system comprises the sulfonates and the heterocyclic amines. Especially preferred sulfonates are the sulfonates of alkyl-substituted benzene, especially toluene.

The process of the invention will be more fully understood by reference to the following examples which are given for illustrative purposes only and are not to be interpreted as limitative of the invention.

EXAMPLE 1

Two grams of zinc trifluoroacetate, 25 ml of acrylonitrile (containing 100 ppm hydroquinone) and 4 ml of triethylamine are charged to a 100 ml glass reactor equipped with a condenser and a magnetic agitator. The reactor is placed in a constant temperature water bath and the mixture is allowed to react for 16 hours at 25°C. The effluent is then analyzed by gas/liquid chromatography for 2-methyleneglutaronitrile (product) and unconverted acrylonitrile. The 2-methyleneglutaronitrile yield is found to be 72.5%. Only a small amount of acrylonitrile trimer along with acrylonitrile polymer are detected as by-products.

In the following examples, as in this example, the dimer is essentially the only product formed and trimer and acrylonitrile polymer, if detectable at all, are present in very small amounts, demonstrating the highly selective nature of the catalyst in producing dimer.

EXAMPLES 2–16

Using the general procedure described in Example 1, a series of experiments are carried out. The feed composition, the reaction conditions and the yield of 2-methyleneglutaronitrile (2-MGN), based on the amount of acrylonitrile charged to the reactor, obtained in these experiments are reported in Table 1.

EXAMPLE 17

Two grams of zinc trifluoroacetate, 25 ml of acrylonitrile (containing 100 ppm of hydroquinone) and 4 ml of triethylamine are charged to a 100 ml stainless steel (316 ss) autoclave equipped with magnetic stirring. The autoclave is connected to a pressure regulator and pressurized with 100 psig of nitrogen. The reactor is placed in a constant temperature oil bath and the mixture is allowed to react for 1 hour at 100°C under a constant system pressure of 100 psig. The effluent is then cooled to room temperature, discharged and analyzed by gas/liquid chromatography. The 2-methyleneglutaronitrile (product) yield is 5% based on the amount of acrylonitrile charged to the reactor.

EXAMPLE 18

Eighty grams of Zn(p-toluenesulfonate)$_2$, 500 ml of acrylonitrile (containing 100 ppm of hydroquinone) and 80 ml triethylamine are charged to a 1 liter reaction flask equipped with thermometer, condenser and stirrer. The reaction flask is placed in a constant temperature water bath and the mixture is allowed to react for 16 hours at 25°C. The effluent is then transferred to a 2-liter separation funnel and extracted with 1080 grams of p-xylene. The p-xylene extract (1300 grams) containing 214 grams of 2-methyleneglutaronitrile (based on gas/liquid chromatographic analysis) is fractionated through a 20-plate Oldershaw column. One hundred and eighty grams of 2-methyleneglutaronitrile are collected as the cut distilling between 144° and 148°C at 20 mm Hg pressure.

B. The experimental procedure described in A is repeated using 10 millimoles of $ZnCl_2$ instead of the $Zn(p$-toluenesulfonate$)_2$. In contrast to the result reported above, the $ZnCl_2$ obtained as the distillation residue is found to have a catalytic activity which is less than 10% of the activity of fresh $ZnCl_2$ catalyst.

TABLE 1

| | | FEED COMPOSITION | | | CONDITIONS | | MGN |
|---|---|---|---|---|---|---|---|
| Example | Acrylonitrile ml. | Lewis base grs. | Salt grs. | Solvent ml. | Time hr. | Temp. °C | Yield % |
| 2 | 25 | Triethylamine 2.9 | Zn(dichloroacetate)$_2$ 5.0 | None | 3 | 60 | 4.5 |
| 3 | 25 | Triethylamine 2.9 | Zn(trichloroacetate)$_2$ 3.0 | None | 16 | 25 | 10.0 |
| 4 | 25 | Triethylamine 2.9 | Co(trifluoroacetate)$_2$ 2.0 | None | 16 | 25 | 12.5 |
| 5 | 25 | Diethylaminomethyl-polystyrene* 4.0 | Zn(trifluoroacetate)$_2$ 2.0 | None | 16 | 50 | 15.0 |
| 6 | 25 | N-methylpiperidine 3.0 | Zn(cyanoacetate)$_2$ 2.0 | None | 16 | 25 | 5.0 |
| 7 | 46 | Triethylamine 6.0 | Zn(p-toluenesulfonate)$_2$ 11.25 | None | 1 | 30 | 50.0 |
| 8 | 25 | N,N-dimethylbenzyl-amine 3.0 | Zn(p-toluenesulfonate)$_2$ 2.0 | None | 18 | 30 | 37.5 |
| 9 | 25 | Tributylamine 3.0 | Zn(p-toluenesulfonate)$_2$ 2.0 | None | 16 | 30 | 8.8 |
| 10 | 25 | N,N,N¹,N¹-tetramethyl-1.6-hexanediamine 3.0 | Zn(p-toluenesulfonate)$_2$ 2.0 | None | 16 | 30 | 11.3 |
| 11 | 25 | N,N-diethylaniline 3.0 | Zn(p-toluenesulfonate)$_2$ 2.0 | None | 16 | 30 | 52.5 |
| 12 | 25 | N,N¹-dimethylpiperazine 3.0 | Zn(p-toluenesulfonate)$_2$ 2.0 | None | 16 | 30 | 60.0 |
| 13 | 23 | Triethylamine 6.0 | Zn(p-toluenesulfonate)$_2$ 11.3 | Sulfolane 23 | 1 | 30 | 50.0 |
| 14 | 23 | Triethylamine 6.0 | Zn(p-toluenesulfonate)$_2$ 11.3 | o-dichlorobenzene 23 | 2.5 | 30 | 50.0 |
| 15 | | Triethylamine 2.9 | Zn($\beta$-naphthalene sulfonate)$_2$ 2.0 | None | 16 | 25 | 15.5 |
| 16 | 25 | Triethylamine | Zn(trifluoromethane sulfonate)$_2$ | None | 16 | 25 | 15.5 |

*Diethylaminomethyl-polystyrene: 3 meqv. of base/gr. resin

As will be seen from the data provided by the foregoing examples, favorable yields of the dimer product can be obtained and a further advantage of the process of the invention is that it provides a non-corrosive reaction system so that equipment can be fabricated from inexpensive materials of construction. Furthermore, the catalysts of this invention, especially the sulfonates, can be recycled for further use with little or no loss of catalytic activity, even when the product is separated by simple distillation, in contrast with the catalyst disclosed in U.S. Pat. No. 3,733,351, for example. This is shown by the following example.

EXAMPLE 19

Comparative experiments (A and B) illustrate the recycling of catalysts.

A. Ten millimoles of Zn(p-toluenesulfonate)$_2$, 50 ml of acrylonitrile (containing 100 ppm of hydroquinone) and 6 ml of N-methyl piperidine are charged to a 100 ml jacketed glass reactor equipped with an agitator and with means for continuously discharging the effluent through the bottom of the reactor. The reaction temperature is controlled by passing constant temperature water through the reactor jacket and the mixture is allowed to react at 40°C until a 2-methyleneglutaronitrile yield of 20% has been obtained. The reaction mixture is then continuously fed from the bottom of the reactor to a rotating evaporator over a period of 10 minutes and flash distilled at 160°C and 10 mmHg pressure. The distillation residue consisting mainly of Zn(p-toluenesulfonate)$_2$ and a small amount of acrylonitrile trimer is tested for catalytic activity in reaction with fresh acrylonitrile and N-methylpiperidine at 40°C. The Zn(p-toluenesulfonate)$_2$ so obtained is found to have practically the same catalytic activity as fresh catalyst.

In the foregoing examples the term "yield" has its usual meaning and can be expressed as follows:

$$\% \text{ yield} = \frac{\text{weight dimer produced}}{\text{weight acrylonitrile charged}} \times 100$$

It will be apparent that various changes and modifications may be made without departing from the invention as defined in the appended claims and it is intended, therefore, that all matter contained in the foregoing description shall be interpreted as illustrative only and not as limitative of the invention.

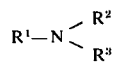

What is claimed is:

1. A process for the dimerization of acrylonitrile to produce 2-methylene glutaronitrile which comprises reacting said acrylonitrile in the liquid phase at a temperature of 10° to 150°C. in the presence of a catalyst consisting essentially of (a) at least one metal compound of the formula $M(X)_n$ wherein M is Zn or Co, X is an anion of an aryl sulfonic acid or of a carboxylic acid containing at least two carbon atoms which is substituted by at least one of the groups, —F, —Cl, —Br, —I and —CN in the $\alpha$-C-position relative to the acid group, and $n$ is a number equal to the valence of the metal M divided by the number of acid equivalents of X; and (b) at least one nitrogen-containing Lewis Base which is (1) a tertiary monoamine of the formula